United States Patent [19]

Watson et al.

[11] Patent Number: 4,822,731

[45] Date of Patent: Apr. 18, 1989

[54] PROCESS FOR LABELING SINGLE-STRANDED NUCLEIC ACIDS AND HYBRIDIZATION PROBES

[75] Inventors: Robert M. Watson, Berkeley; Edward L. Sheldon, III; Richard M. Snead, both of Oakland, all of Calif.

[73] Assignee: Cetus Corporation, Emeryville, Calif.

[21] Appl. No.: 819,490

[22] Filed: Jan. 9, 1986

Related U.S. Application Data

[63] Continuation-in-part of Ser. No. 716,975, Oct. 25, 1985

[51] Int. Cl.$^4$ ............................................... C12Q 1/68
[52] U.S. Cl. ................................................ 435/6; 435/7; 436/501; 436/827; 536/27; 935/78
[58] Field of Search ............... 435/6; 935/78; 436/501, 436/827; 536/27

[56] References Cited

U.S. PATENT DOCUMENTS

| | | |
|---|---|---|
| 4,124,598 | 11/1978 | Hearst et al. |
| 4,358,535 | 11/1982 | Falkow et al. |
| 4,542,102 | 9/1985 | Dattagupta et al. ............ 435/6 |
| 4,563,417 | 1/1986 | Albarella et al. |
| 4,581,333 | 4/1986 | Kourilsky et al. |
| 4,582,788 | 4/1986 | Erlich ........................ 435/6 |
| 4,582,789 | 4/1986 | Sheldon et al. |
| 4,617,261 | 10/1986 | Sheldon et al. ............... 435/6 |
| 4,683,195 | 7/1987 | Mullis et al. ................. 435/6 |

FOREIGN PATENT DOCUMENTS

| | | |
|---|---|---|
| 0063879 | 3/1982 | European Pat. Off. |
| 0131830 | 1/1985 | European Pat. Off. |
| 8502628 | 6/1985 | PCT Int'l Appl. |

OTHER PUBLICATIONS

Sood et al., PNAS, 78, 616-620 (1981).
Ploegh et al., PNAS, 77, 6081-6085 (1980).
Brown et al., GENE, 20, 139-144 (1982).
Manning et al., CHROMOSOMA, 53, 107 (1975).
Langer et al., Proc. Natl. Acad. Sci. USA, 78, 6633-6637 (1981).
Leary et al., Proc Natl. Acad. Sci. USA 80, 4045-4049 (1983).
Song et al., ANYAS (1980) 355-67.
Hyde et al., Biochemistry, 17 (1978) 1251-7.
Saffran et al., Proc. Natl. Acad. Sci. U.S.A. 79, 4594-4598 (1982).
V. G. Dev et al., Lancet (England) 1, 1285 (Jun. 10, 1972).
Schwartz et al., Cold Spring Harbor Laboratory Symposium XLVII, pp. 189-195.

*Primary Examiner*—Christine M. Nucker
*Assistant Examiner*—Karen Krupen
*Attorney, Agent, or Firm*—Kevin R. Kaster; Janet E. Hasak; Albert P. Halluin

[57] ABSTRACT

Nucleic acids may be labeled by complexing the alkylating moiety of a labeling reagent into a single-stranded nucleic acid to form a complex and activating the complex to cause covalent bonding between the reagent and the nucleic acid. Preferably, the labeled nucleic acid is a single-stranded hybridization probe for detecting nucleic acid sequences capable of hybridizing with a hybridizing region of the nucleic acid. Also preferably the label moiety is non-radioactive. The labeling reagent is of the formula:

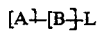

where A is an alkylating moiety, B is a divalent organic moiety of the formula:

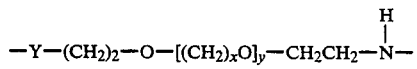

where Y is O, NH or N—CHO, x is a number from 1 to 4, y is a number from 2 to 4, and L is a monovalent label moiety, wherein B is exclusive of any portion of the alkylating and label moieties.

Preferably A is a 4-methylene-substituted psoralen moiety, and most preferably A is a 4'-methylene-substituted-4,5',8-trimethylpsoralen moiety and L is biotin.

28 Claims, 3 Drawing Sheets

RESTRICTION MAP OF M13mp9CHL2.1

FIG. 3

M13mp9 CLONING REGION

```
   1   2   3   4     1   2   3   4   5   6   7   8   9  10  11      5   6   7   8
  Thr Met Ile Thr   Pro Ser Leu Ala Ala Gly Arg Ile Pro Gly         Asn Ser Leu Ala
A ATG ACC ATT ACG   CCA AGC TTG GCT GCA GGT CGA CGG ATC CCC GGG     AAT TCA CTG GCC
                        HindIII          PstI          BamHI  SmaI  EcoRI
                                              SalI           Xmal
                                              AccI
                                              HindII
                                              HincII
```

M13mp10 CLONING REGION

```
   1   2   3   4   5   6     1   2   3   4   5   6   7   8   9  10  11  12  13  14  15  16     7   8
  Thr Met Ile Thr Asn Ser   Ser Ser Pro Gly Asp Pro Leu Glu Ser Thr Cys Ser Pro Ser Leu Ala    Leu Ala
B ATG ACC ATT ACG AAT TCG   AGC TCG CCC GGG GAT CCT CTA GAG TCG ACC TGC AGC CCA AGC TTG        CTG GCC
          EcoRI SacI            XmaI BamHI     XbaI         SalI   PstI                HindIII
                                Smal                         AccI
                                                             HincII
```

PROCESS FOR LABELING SINGLE-STRANDED NUCLEIC ACIDS AND HYBRIDIZATION PROBES

Related U.S. application Data Continuation-in-part of Ser. No. 716,975, Oct. 25, 1985.

BACKGROUND OF THE INVENTION

This invention relates to a means of labeling single-stranded nucleic acids, preferably DNA. More particularly, this invention is directed to a process for preparing labeled single-stranded nucleic acids by use of an alkylating agent containing a label moiety, where the word label is intended to include moieties which may be detected both directly and indirectly. In addition, this invention relates to a means for detecting the presence of a nucleic acid sequence such as a gene or mRNA using a labeled single-stranded hybridization probe containing a complementary nucleic acid sequence.

In biomedical research and recombinant DNA technology it is often useful to have indicator probes which allow the user to detect, monitor, localize or isolate nucleic acids when present in any amount. Hybridization probes, for example, contain a nucleic acid sequence complementary to the nucleic acid sequence or to the gene to be detected. Such probes have been used to detect the presence of genes coding for antigens responsible for graft rejection, such as cell anemia. For example, Sood et al., *PNAS*, 78, 616–620 (1981) describe the isolation of cDNA clones for HLA-B antigens. These clones were prepared by synthesizing cDNA from an mRNA mix containing mRNA coding for the desired HLA antigen, inserting the cDNA into a vector, transforming a bacterial host and isolating transformant clones that contain the desired DNA segment by probing with an oligonucleotide probe that is specific for the desired DNA sequence. Ploegh et al., *PNAS*, 77, 6081–6085 (1980) have also reported cloning a cDNA probe for an HLA gene sequence. In addition, U.S. Pat. No. 4,358,535 to Falkow et al. describe a method for detecting infectious disease-causing microbes using labeled nucleotide probes complementary to nucleic acid contained by the pathogenic microbe. Until recently, the materials most sensitive and therefore useful for this purpose were radioactively labeled nucleic acids such as those labeled with isotopes of, e.g., hydrogen ($^3$H), phosphorus ($^{32}$P) or iodine ($^{125}$I). Brown et al., *Gene*, 20, 139–144 (1982) teaches stabilizing radioactive RNA-DNA hybridization probes using trimethylpsoralen.

Such radioactive compounds, however, suffer from various drawbacks, including extensive safety precautions, expensive equipment, health-monitoring services and waste treatment, and high usage costs due to the instability of the materials. Therefore, there is an increasing incentive to search for suitable nonradioactive labels for nucleic acids which would provide sensitive probes.

Already known is that haptens can initiate an immune response if bound to a carrier, so as to be useful for labeling and identification. Thus, for example, hapten-labeled DNA can be detected with antibodies.

Methods have been developed using non-radioactive biotinavidin complexes for visually localizing specific proteins, lipids or carbohydrates on or within cells and for labeling DNA. For example, Manning et al., *Chromosoma*, 53, 107 (1975) have determined the chromosomal location of ribosomal genes by electron microscopy using a biotinylated protein, cytochrome C, chemically crosslinked to RNA as a hybridization probe. Langer et al., *Proc. Natl. Acad. Sci. USA*, 78, 6633–6637 (1981) describe a method for labeling DNA by enzymatic incorporation of nucleotide analogs containing functional groups such as biotin via DNA polymerase I, and Leary et al., *Proc. Natl. Acad. Sci. USA*, 80, 4045–4049 (1982) have used this method to label DNA probes with biotinylated nucleotides. Also, it is well known how to attach chemical moieties to pyrimidine and purine rings using an acetoxymercuration reaction whereby covalently bound mercury atoms are introduced into the 5-position of the pyrimidine ring, the C-8 position of the purine ring, or the C-7 position of a 7-deazapurine ring. European Patent Publication No. 0,063,879 to Ward et al. describes the preparation of a nucleotide derivative by a process where a mercurated intermediate is formed which reacts with a reactive chemical moiety which may be the label or which then reacts with the labeled compound. The derivative contains biotin, iminobiotin, lipoic acid or other label attached covalently to the pyrimidine or purine ring which will interact with proteins such as avidin or antibodies. When biotin is bound specifically by an avidin-linked enzyme complex, detection is seen as a color change in a chromogenic substrate. When an avidin-alkaline phosphatase complex is used to detect biotinylated DNA probes after hybridization, sensitivity has been shown to approach that of autoradiography used to detect $^{32}$P labeled probes. In this method, the labeled nucleotide is then enzymatically incorporated into the DNA so that the DNA probe is labeled.

Methods also exist for studying the molecular structure of DNA. For example, psoralens, which are a class of planar furocoumarin molecules capable of intercalating into double-stranded DNA in the presence of single-stranded DNA, will covalently bond to as well as crosslink DNA when activated by long-wave (>350 nm) UV light. Covalent bonding involves a two-step process: (1) initial noncovalent binding of the planar-structured psoralen to the bases of the nucleic acid to produce a psoralen-nucleic acid complex and (2) irradiation of the complex with light of the proper wavelength to form covalent bonds between the psoralen molecules and pyrimidine nucleotides which occur as integral entities of nucleic acid strands.

This covalent bonding enables the study in vivo of secondary structures of DNA such as packaging of nucleic acid within viruses. Use of 4'-adducts of 4,5',8-trimethylpsoralen to bond DNA covalently is described in U.S. Pat. No. 4,124,598 to Hearst et al. Hearst, Rapoport and others have extensively studied the incorporation of psoralens into DNA and RNA. Song et al., *ANYAS* (1980) 355–67 and Hyde et al., *Biochemistry*, 17 (1978) 1251–7 disclose use of psoralen compounds to study secondary structures.

Schwartz et al., CSH Laboratory Symposium XLVII discloses DNA crosslinking with DNA or proteins using various psoralen containing compounds. Saffran et al., *Proc. Natl. Acad. Sci. U.S.A.*, 79, 4594–4598 (1982) describes use of one of these compounds containing a thiol group for site-directed psoralen crosslinking of DNA to enable structural analysis of DNA. In this process the plasmid DNA molecule has mercurated nucleotides incorporated near a restriction site so that the psoralen is directed to the bases through a Hg-S linkage. Use of mercurated compounds in reaction syntheses involves extra expense and necessitates safety precautions in view of the toxicity of mercury.

U.S. Pat. No. 4,547,569 issued Oct. 15, 1985, which is a continuation-in-part of Ser. No. 444,438, filed Nov. 24, 1982, now abandoned, to Letsinger et al. describes bifunctional intercalators containing a phenanthridium moiety as an agent for introducing markers (e.g., fluorescent probes) at specified regions in polynucleotides, presumably for determining secondary structure.

In addition to their use in studying nucleic acid secondary structure, commercial applications of the psoralen derivatives include their use in treating certain dermatological disorders and for viral inactivation to produce vaccine.

Another use for compounds which label DNA is in chromosome banding or staining. An example described in the literature is the use of the Giemsa reagent to stain regions or bands of chromosomes differentially, as described in the article by V. G. Dev et al., *Lancet* (England) 1, 1285 (June 10, 1972). Because chromosomes have characteristic banding patterns, this procedure can be used to distinguish chromosomes. This ability to distinguish chromosomes has been very useful in the study of chromosome anomalies. For example, Down's syndrome can be diagnosed by determining that the individual is trisomic for chromosome 21.

European Patent Publication No. 131,830 discloses in minimal detail use of alkylating intercalators to label single- and double-stranded nucleic acids. PCT No. WO85/02628 published June 20, 1985 discloses single-stranded hybridization probes carrying labeled molecules capable of forming covalent crosslinks between the single-stranded region of the probe and the target molecules. U.S. Pat. Nos. 4,582,789 and 4,617,261, issued Apr. 15, 1986, and Oct. 14, 1986, respectively, disclose labeling the double-stranded region of partially double-stranded nucleic acids with the labeling reagents used in this invention, but do not disclose the labeling of single-stranded nucleic acids.

SUMMARY OF THE INVENTION

To obviate the disadvantages associated with the labeled probes presently existing, the present invention provides an enabling means for producing simple, stable, labeled single-stranded nucleic acid hybridization probes which, rather than using mercurated intermediates or enzymes, employs specific labeling compounds capable of both non-covalent and covalent binding to introduce label moieties into single-stranded nucleic acids. Such probes do not require the several preparation steps which may be required to produce partially double-stranded probes, yet are workable probes.

As a further advantage the method herein is preferably employed to label single-stranded nucleic acids nonradioactively to avoid the disadvantages of radioactive labeling.

Specifically, the invention herein relates to a process for labeling a single-stranded nucleic acid which comprises the steps of:

(a) contacting the single-stranded nucleic acid with one or more labeling compositions of the formula:

[A]—[B]—L wherein A is an alkylating moiety, B is a divalent organic moiety having the formula:

$$-Y-(CH_2)_2-O-[(CH_2)_xO]_y-CH_2CH_2-\overset{H}{\underset{|}{N}}-$$

where Y is O, NH or N—CHO, x is a number from 1 to 4 and y is a number from 2 to 4, and L is a monovalent label moiety, wherein B is exclusive of any portion of the alkylating and label moieties, said contacting occurring so as to cause the alkylating moiety of the labeling composition to complex with the nucleic acid; and (b) activating the complex so as to induce the alkylating moiety to bond covalently to the nucleic acid.

Preferably the alkylating moiety is 4'-methylene-substituted psoralen.

The labeled nucleic acids thus prepared may be used in a marker mix if two or more so labeled nucleic acids of different length or specificities are mixed together.

In another aspect, the invention relates to a process for preparing a labeled nucleic acid hybridization probe for detecting homologous nucleic acid sequences which process comprises the steps of:

(a) contacting a single-stranded nucleic acid comprising a region capable of hybridization with the nucleic acid sequence to be detected, with at least one of the labeling compositions described above, said contacting causing the alkylating moiety of the labeling composition(s) to complex with the nucleic acid; and (b) activating the complex to induce the alkylating moiety to bond covalently to the nucleic acid.

Preferably these processes are carried out using nonradioactively labeled reagents.

The invention also includes the hybridization probe itself comprising a single-stranded nucleic acid having the hybridization region described above, where the probe is covalently bound to one or more alkylating moieties and where the alkylating moiety is bound to a divalent organic moiety which is in turn bound to the label moiety. The divalent organic moiety is of the formula:

$$-Y-(CH_2)_2-O-[(CH_2)_xO]_y-CH_2CH_2-\overset{H}{\underset{|}{N}}-$$

where Y is O or NH or N—CHO, x is a number from 1 to 4, and y is a number from 2 to 4.

In a further aspect the invention provides a process for detecting the probe comprising exposing and separating the nucleic acid strands of the sample being analyzed, contacting the strands with a hybridization probe, and detecting whether hybridization of homologous nucleic acid sequences to the probe has occurred by means of the label moiety on the probe. This may be accomplished by exposing the probe after hybridization to a means by which the label moiety of the probe is capable of being identified, and identifying the label moiety using an appropriate identification technique. Examples of such techniques include spectroscopic, radioisotopic, photochemical, chemical, immunochemical or biochemical means as by using a polypeptide, lectin or antibody capable of forming a complex with the label moiety of the probe. Using the preferred biochemical means, the probe is contacted with a polypeptide, lectin or antibody capable of forming a complex therewith under suitable conditions so as to form the complex, said polypeptide, lectin or antibody being capable of or including a label which can be detected when the complex is formed, and the complex is detected using an appropriate technique.

In yet another embodiment of the invention, one or more nucleic acid sequences, preferably those characteristic of a pathogenic microbe or associated with an amplified oncogene, HLA typing or a genetic disease, are detected by a process comprising:

(a) contacting a sample containing the nucleic acid(s) to be detected (which sample generally consists of cells, body fluid or viral or tissue sample) with an effective amount of reagent sufficient to expose the nucleic acids in the sample (e.g., to open the cells, body fluid, viral capsids, or tissue of the sample) and to separate the strands of the nucleic acid(s);

(b) depositing the sample before, during, or after step (a) on a support;

(c) contacting the deposited sample with an effective amount of reagent sufficient to affix a substantially single-stranded of the nucleic acid(s) on the support;

(d) contacting the affixed single-stranded nucleic acid with an effective amount of the hybridization probe as described above under hybridization conditions; and (e) detecting hybridization of any homologous single-stranded nucleic acid sequences by means of the label moiety on the probe.

BRIEF DESCRIPTION OF THE DRAWINGS

FIG. 3 represents the cloning region of M13mp9 (FIG. 3A) and the cloning region of M13mpIO (FIG. 3B).

DESCRIPTION OF THE PREFERRED EMBODIMENTS

Figure 1:
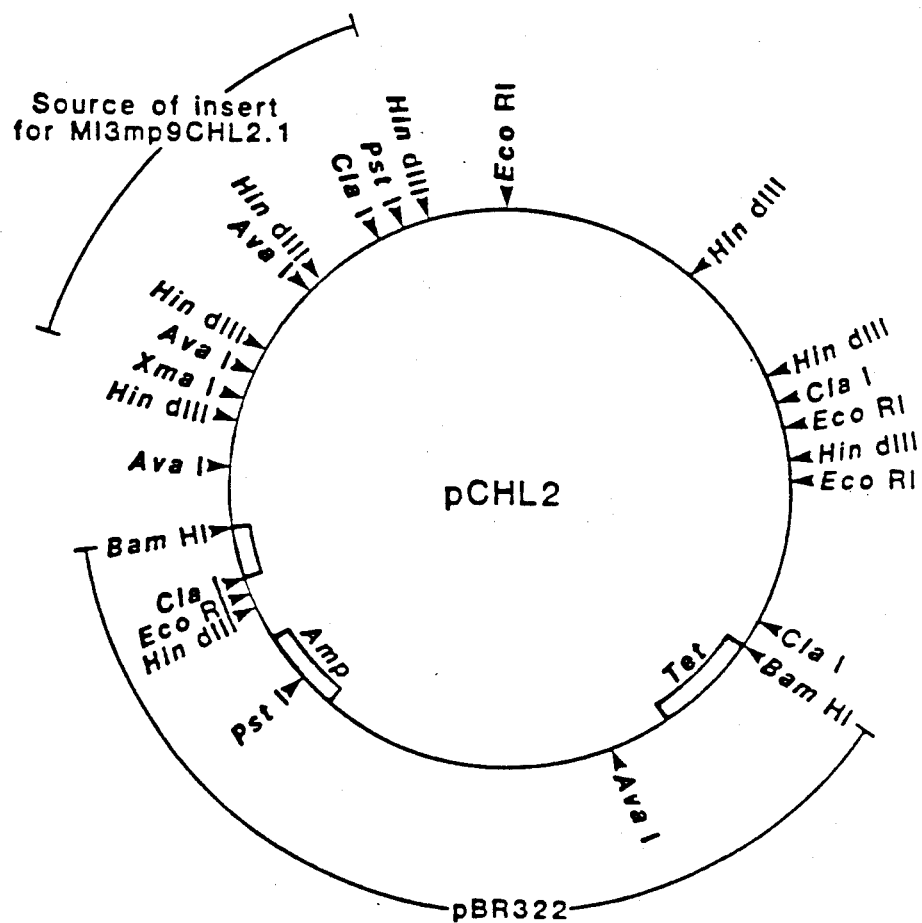
FIG. 1 represents a restriction map of pCHL2, a *Chlamydia trachomatis* plasmid cloned into the BamHI site of pBR322. The M13mp9CHL2.1 subclone of pCHL2 is an approximately 1500 base pair insert between the XmaI and PstI restriction sites as indicated.

The following terms as used in the specification and claims have the following definitions:

"Spacer arm" refers to a divalent organic moiety which is chemically non-reactive with the alkylating moiety and label moiety employed herein and contains no portion of either and is of the formula:

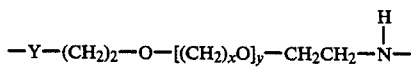

where Y is O, NH or N—CHO, x is 1 to 4 and y is 2 to 4. Preferably Y is O or NH, x is 2 and y is 2. The purpose of the spacer arm is to provide a chemical linkage between the alkylating moiety and the label moiety so that the label can readily interact with such detection means as antibodies, other detector polypeptides, or chemical reagents without interference. The number of atoms in the straight (main) chain of the spacer arm generally depends on the particular label moiety employed. The chain must be sufficiently long to permit access of a detector complex to the label moiety, i.e., to avoid interference by the nucleic acid. The molecular weight limits of the spacer arm (the values of x and y) will be determined by the types of atoms contained therein and by solubility considerations. As the molecular weight of, for example, polyethylene glycol increases, the spacer arm derived therefrom becomes less water soluble at room temperature and becomes more waxy. Thus, it is less useful in the present invention. The maximum molecular weight for the spacer arm is generally about 1000 to ensure adequate water solubility and fluidity thereof.

"Label moiety" refers to a monovalent moiety which is capable of producing a detectable signal, i.e., which can be detected in small quantities by detection means which generate a signal. Examples of suitable such means include spectroscopic or photochemical means, e.g., fluorescence or luminescence, or biochemical, immunochemical, or chemical means such as changes in physical, biochemical, immunochemical or chemical properties on contact with a detector analysis compound or reaction with a polypeptide or polypeptide/enzyme mixture to form a detectable complex. Thus, as used herein the term "label" is intended to include both moieties that may be detected directly, such as radioisotopes or fluorochromes, and reactive moieties that are detected indirectly via a reaction which forms a detectable product, such as enzymes that are reacted with substrate to form a product that may be detected spectrophotometrically. It is noted that the labeling reagent may contain a radioactive label moiety such as a radioisotope, but the preferred hybridization probe herein is nonradioactively labeled to avoid the disadvantages associated with handling radioactive compounds.

"Body fluid" refers to fluid derived from a human or animal body or from a plant, such as, e.g., blood serum, cerebrospinal fluid, amniotic fluid, urine, and the like.

"Tissue" refers to biological tissue extract material which is not necessarily cellular by definition.

"Alkylating moiety" refers to moieties which initially complex (bind non-covalently) with the nucleic acid. Upon activation the alkylating moiety may or may not covalently bond to the nucleic acid single strand. Such a moiety can form a covalent bond with the bases of the nucleic acid without intercalation occurring. Examples of suitable alkylating compounds from which the moieties are derived include mitomycin C as described by Lown et al., *Can. J. Biochem.*, 54, 110ff (1976), carzinophilin A as described by Lown et al., *J.A.C.S.*, 104, 3213–3214 (1982), 3,5-diazido-5-ethyl-6-phenylphenanthridinium as described by Woolley et al., *Biochemistry*, 22, 3226–3231 (1983), psoralen compounds and derivatives thereof, and other compounds which can be devised which have structures allowing complexing to occur. The preferred moieties herein do not covalently bind, or, if they do, are 4'-methylene-substituted psoralen moieties such as those derived from psoralen compounds described and sold by HRI Associates, Inc., of Emeryville, Calif. via their Oct. 1, 1983 price schedule. The 4'-methylene group is present to act as a link with the spacer arm. Examples of such suitable psoralen moieties include 4'-methylene-substituted psoralen, 4'-methylene-substituted-5-methoxypsoralen, and 4'-methylene-substituted-4,5',8-trimethylpsoralen. The most preferred psoralen moiety herein is 4'-methylene-substituted-4,5',8-trimethylpsoralen.

"Activation of the complex of alkylating moiety and nucleic acid" refers to means used to induce the alkylating moiety of the labeling reagent to bond covalently to the nucleic acid strand. The appropriate activation means will depend mainly on the type of alkylating moiety being employed. For example, the psoralen moieties and the moiety derived from 3,5-diazido-5-ethyl-6-phenylphenanthridinium will require activation by irradiation with ultraviolet light. Mitomycin C will form a complex activated by reduction thereof. Carzinophilin A will form a complex activated by protonation (acid activation) thereof. Thus, any means appropriate to the type of moiety employed for the reagent may be utilized for this purpose.

The label moiety of the labeling reagent herein is capable of producing a signal which can be detected by detection means. Examples of such detection means include spectroscopy, such as fluorescence and luminescence, photochemistry, radioactivity, biochemical means, immunochemical means, chemical means, and the like. Preferred means include forming a detectable complex with a polypeptide, lectin or antibody in the presence or absence of an enzyme associated with the polypeptide, lectin or antibody. Depending on the label moiety employed, an example of a polypeptide useful for this purpose is avidin or streptavidin complexed with an enzyme when biotin is the label moiety. Suitable antibodies would include, e.g., antibiotin antibodies or antidinitrophenol antibodies if the label moiety is dinitrophenol. Lectins, which are glycoproteins, would be employed as the detection means if carbohydrates are used as label moieties.

The detection means, if it is an antibody, a lectin, or some other polypeptide capable of complexing with the label moiety, would be linked to an entity capable of generating a detectable change. Examples of such entities include enzymes such as, e.g., alkaline phosphatase, which has chromogenic or fluorogenic substrates, or luciferase, which can generate luminescence. The label moiety may be any group possessing the detection properties described above, including haptens, which are only immunogenic when attached to a suitable carrier, but are capable of interacting with appropriate antibodies to produce detectable complexes.

Examples of suitable label moieties include those of the formulae:

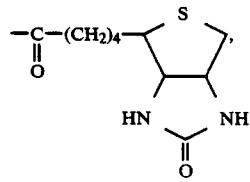

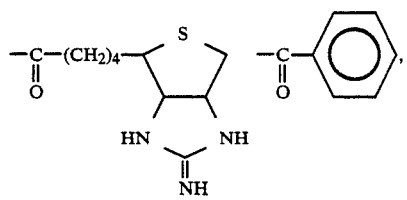

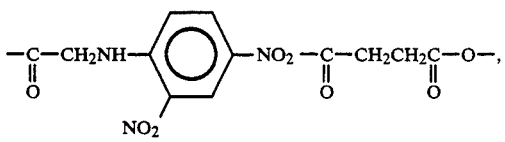

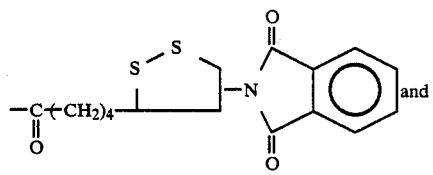

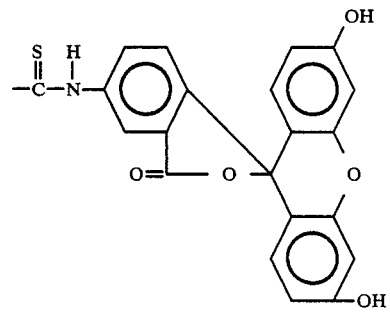

As label moieties containing aromatic groups tend to intercalate into nucleic acid(s), the preferred label moiety is nonaromatic, and the most preferred label moiety is biotin.

Examples of preferred labeling reagents for preparing the probes of this invention include:

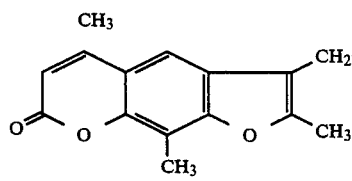 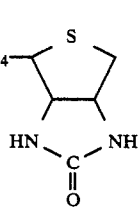

where R and R' are independently —H;

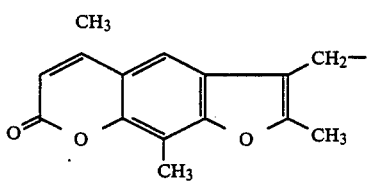 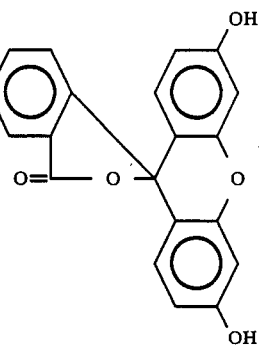

where R and R' are as defined above;

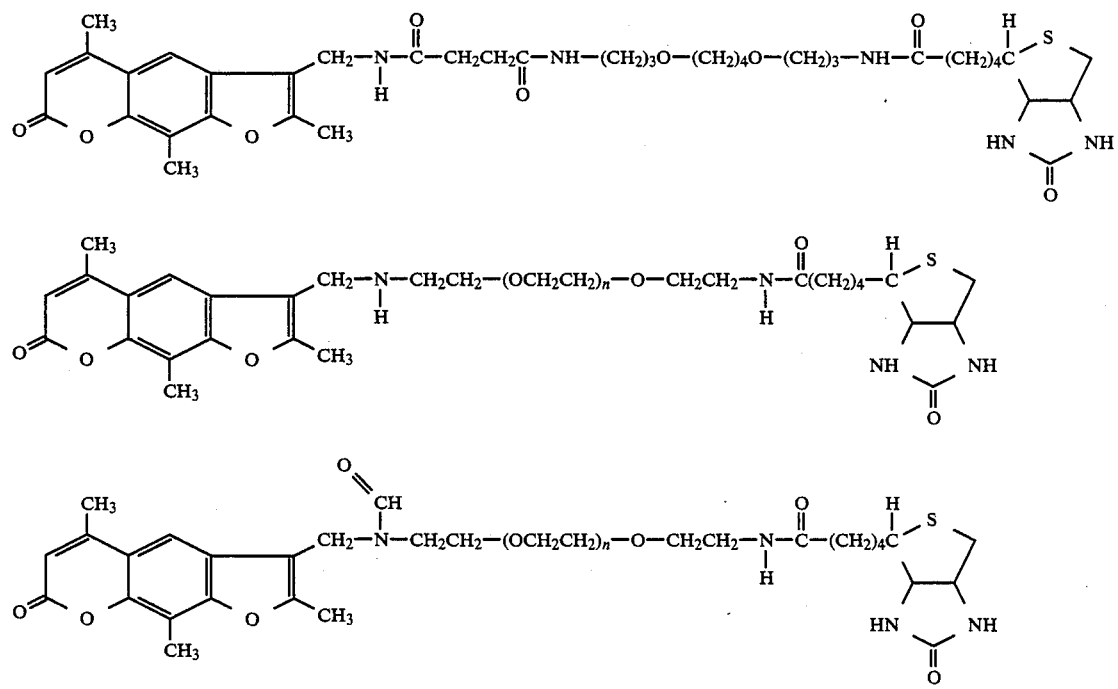

and

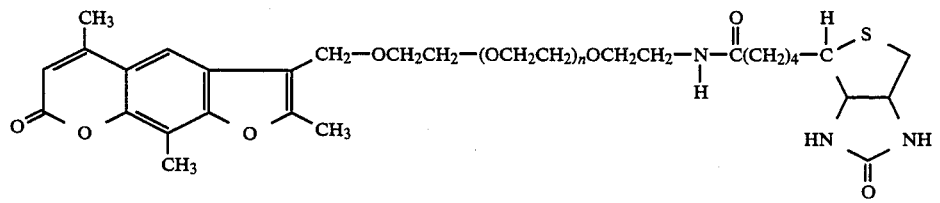

wherein n is an integer of from 1–4, and most preferably 2. The compounds where n is 2 are the most preferred, because they are easy to prepare and exhibit improved incorporation into DNA. The third-to-last-named and the last-named derivatives where n is 2 are particularly preferred.

The above-described reagents may be prepared by various methods already described in U.S. Pat. No. 4,582,789, issued Apr. 15, 1986, the disclosure of which is incorporated herein by reference, and in the examples which follow.

The last named compound, 1-(biotinylamino)-13-(4,5',8-trimethylpsoralen-4'-yl)-3,6,9,12-tetraoxa-tridec-ane, which is not specifically described in the copending application, is prepared by a method wherein tetraethylene glycol, or the appropriate polyethylene glycol for higher homolog chains, is reacted with para-toluene sulfonyl chloride in pyridine to yield the mono-tosylate alcohol, which when heated with lithium azide affords the corresponding azido alcohol, which in turn is reduced to the corresponding amino alcohol. The amino alcohol is then converted to the mono-tertbutyloxy carbonyl protected derivative using di-tert-butyl dicarbonate in tetrahydrofuran. The protected derivative is then reacted with chloromethyl trioxsalen to yield the psoralen derivative:

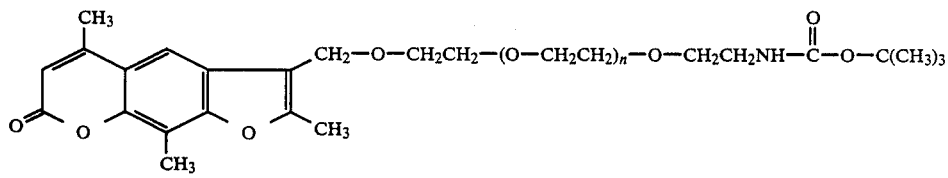

where n is 2 if tetraethylene glycol was employed initially. This compound, in the presence of trifluoroacetic acid in acetonitrile in the dark, becomes the primary amine terminated precursor as described above, which can then be reacted with, e.g., the N-hydroxysuccinimide ester of biotin or another appropriate label.

One useful application of the reagents described above is in labeling single-stranded nucleic acids. Generally this technique involves two steps: (1) contacting the nucleic acid with one or more of the reagents in such a way as to cause the alkylating moiety thereof to form a complex between the two, and (2) activating the complex in such a manner that the alkylating moiety of the reagent bonds covalently to the single nucleic acid strand.

The first step is preferably carried out by incubating the nucleic acid with the reagent(s) at about 0 to 50° C., preferably about 4 to 20° C., in a medium containing a buffer and having a pH of between about 6 and 9, preferably between about 6 and 8. The incubation generally will not require more than about 10 minutes. The buffer may consist of any buffer useful for this purpose such as, e.g., 10 mM Tris-HCl at pH 7.0 and 1 mM EDTA.

After the nucleic acid has been incubated for a sufficient period of time to complex with the alkylating agent, the nucleic acid containing complex is, in the same medium, activated by such means as, e.g., reduction, irradiation, protonation or the like, depending on the alkylating moiety, for a sufficient period of time and under suitable conditions to ensure covalent bonding. The skilled practitioner will recognize what particular conditions are necessary given a particular moiety whose alkylating properties are described in the art. If the moiety is a psoralen derivative, for example, the complex is irradiated with UV light, preferably at about 350 to 390 nm wavelength, and more preferably at about 360 nm, at 1 to 100 mWatts per $cm^2$ for from 1 minute to 15 hours, to ensure covalent bonding.

The resultant nucleic acids will be labeled so that the label moiety can be detected by, for example, spectroscopic, photochemical, chemical, immunochemical or biochemical means. Thus, the labeled nucleic acid(s) may be subjected to, e.g., ultraviolet light to stimulate fluorescence or contacted with a polypeptide, lectin or antibody depending on the label moiety in the labeling reagent. In addition, the detection means may consist of a combination of an absorber-emitter moiety and a chemiluminescent catalyst in sufficiently close proximity to each other to permit non-radioactive energy transfer, in conjunction with chemiluminescent reagents suitable for inducing a light response in the presence of the chemiluminescent catalyst, as described in European Patent Publication No. 0,070,686 published Jan. 26, 1983 and in European Patent Publication No. 0,070,685 published Jan. 26, 1983. Preferably the detection means is non-radioactive to obviate the difficulties associated with radioactive probes.

The degree of incorporation of these labeling reagents into nucleic acids can be measured by introducing a tritium atom into the compound as described in the experimental section. Nucleic acid incorporation of tritiated reagents can be determined by liquid scintillation counting or by autoradiography, which detection techniques are known in the art.

The nucleic acid itself which may be labeled by this technique may be any single-stranded nucleic acid such as single-stranded DNA or RNA. Preferably the nucleic acid is DNA. More than one type of single-stranded nucleic acid may be present in the incubation broth for complexing and alkylation.

A particularly useful application for the process herein is in preparing a labeled single-stranded nucleic acid hybridization probe (preferably non-radioactively labeled) for detecting nucleic acid sequences (RNA and/or DNA) such as, e.g., those characteristic of a pathogenic microbe or those responsible for or linked to a genetic disease. Pathogens would include infectious disease causing microorganisms or microorganisms involved in food spoilage. The probe may be a single-stranded M13 probe containing a hybridization region which will act to detect by hybridization the nucleic acid sequence desired. A DNA of the latter description may be prepared by the method described by Brown et al., *Gene*, 20, 139–144 (1982) where a DNA fragment of the hybridizing region complementary to the sequence to be detected is inserted into the double-stranded form of a virus known as M13, which is publicly available, at a restriction site therein. After transformation, a single-stranded form of M13 is prepared containing the hybridizing region which is complementary to the sequence to be detected.

More specifically, in this process the M13 phage enters the bacterial host cell via pilus and single-stranded DNA is converted to the transient M13 replicative form (RF) double-stranded DNA, which is used as a cloning vector. A fragment of DNA from any source, preferably a cloned foreign DNA fragment, is inserted into a suitable restriction enzyme site in the cloning region within the M13 RF DNA after the RF DNA is cleaved with the appropriate restriction enzyme. M13 RF DNA carrying such a double-stranded insert is introduced into a suitable competent host cell such as *E. coli* by a transformation step. Growth of the host produces the hybrid molecule in both double-stranded and single-stranded (mature virus) forms. The single-stranded form with the cloned insert is then separated by separate culturing and isolated. This cloning procedure is described in more detail by Messing, J. (1981) *Third Cleveland Symposium on Macro-Molecules:Recombinant DNA*, Ed. A. Walton, Elsevier, Amsterdam, p. 143–153, and summarized in the Amersham Corporation publication entitled "M13 Cloning and Sequencing Handbook" (5/83) beginning at page 8. The probes thus obtained are then subjected to complexing and alkylation with the labeling reagent as described above.

The probes herein can be used to detect any nucleic acid sequence to which the probe can hybridize, including specific nucleotide sequences of bacterial, viral, fungal, yeast, mammal, or parasite origin in samples such as food or clinical samples, whether located in chromosomes, fixed cells, animal cell membranes, body fluids, viral samples, bacterial cell walls or membranes, or tissue sections. When the presence of a specific nucleic acid molecule is ascertained by the probe, one can diagnose an etiological agent in a patient. Examples of organisms which might be detected by the probe herein include *Chlamydia trachomatis, Neisseria gonorhoeae*, toxicogenic *E. coli* organisms, etc. The probe herein also provides a method for screening bacteria to determine antibiotic resistance.

The process herein can also be used to detect genetic diseases such as HLA-linked diseases, thalassemias and sickle cell anemia. The deoxyribonucleic DNA sequence whose presence or absence (in the case of some thalassemias) is associated with the disorder can be detected following hybridization with the probe herein using appropriate detection means.

In addition, the process herein may be used to detect amplified genes such as amplified oncogenes correlated with a particular stage of a disease. For example, N-myc may be able to be detected in the Phase I early cancer stage where the tumor is confined to the organ or structure of origin. See Brodeur et al., *Science*, 224:1121-1124 (1984).

Hybridization can also be used to determine paternity. In addition, the probes herein may be used for research in genetic engineering, e.g., gene mapping (cytogenetics) by in situ blotting hybridization methods, gene walking, subcloning, colony screening and phage screening.

In addition, the probe herein represents a useful research tool in analyzing target nucleic acids, especially DNA. The details of these various methods to which the probe may be applied are described further in European Patent Application No. 0,063,879 to Ward et al. In addition, it may be used to screen lambda libraries.

The method by which the nucleic acid sequences are detected may be any method utilizing hybridization in conjunction with label detection of the probe. For example, the detection may be via a liquid hybridization assay method as described, e.g., in European Patent Publication No. 0,070,687 published Jan. 26, 1983 or in European Patent Publication No. 0,070,685 published Jan. 26, 1983, the entire disclosures of which are incorporated herein by reference. Alternatively, the detection may be by solid phase hybridization as described in U.S. Pat. No. 4,358,535, the entire disclosure of which is incorporated herein by reference, wherein the single-stranded nucleic acid sequence to be detected is affixed to a support and hybridized with the probe. If the process involves HLA typing, genomic DNA from an individual is digested with a restriction endonuclease which produces a polymorphic digestion pattern with HLA DNA and the digest is subjected to gel electrophoresis. The product of gel electrophoresis is then transferred to a support such as a membrane and the following general procedure is employed.

Using either assay method, the sample consisting of cells, animal cell membranes, body fluids, tissues, viral capsids in a viral sample, or bacterial cell walls or membranes is contacted with an amount of a reagent effective to open the cells, membranes, tissues, capsids or cell walls and to expose and separate the strands of the nucleic acid(s). The probe is contacted with the exposed sample under hybridization conditions, and any hybridization product is detected by appropriate means such as, e.g., formation of a soluble or insoluble reaction product.

If solid phase hybridization is employed, the nucleic acid containing sample is placed on a support, which may be contacted with a nutrient source such as a nutrient-containing agar to expand the number of cells to form distinct colonies. The lysing and nucleic acid denaturing step to expose and separate the strands may be conducted before, during, or after the sample is deposited on the support. Thus, for example, the sample may be treated with reagent after it is applied to the support, or it may be mixed with the reagent and then applied to the support, or the support may be impregnated with or placed on or in the reagent before the cell, membrane, body fluid, viral, bacterial or tissue sample is deposited thereon. The support on which the sample is deposited is preferably a water-insoluble porous support, and more preferably a filter such as, e.g., nitrocellulose or a charged or derivatized nylon membrane. The preferred support is a microfilter which inhibits passage of the sample through the filter.

If the sample is first deposited on the support, as by spotting or spreading, the lysing step with reagent is preferably conducted such that the sample does not migrate and remains affixed at the site on the support where it was deposited. One way to accomplish the lysing is to place the support, isolate side up, onto a bibulous support saturated with the lysing reagent for a time sufficient to open the cells, membranes, body fluid, viral, bacterial or tissue sample and separate the strands of the nucleic acid(s). The preferred lysing agent herein is a base, more preferably dilute aqueous solutions of sodium hydroxide, because it also denatures the nucleic acid(s). Other reagents or factors which cause denaturing include organic reagents such as, e.g., alcohols, amides, ureas, phenols, sulfoxides, and the like, certain inorganic ions such as thiocyanate or perchlorate, and elevated temperatures. The concentration and amount of reagent employed for this purpose will depend on whether the nucleic acids are DNA, RNA or hybrids of DNA and RNA.

In the next basic step of solid phase hybridization, a substantially (e.g.,.at least 80%) single-stranded form of the nucleic acid or acids is affixed on the support. Before the fixation step, however, a neutralization step is preferably carried out wherein generally the inert support is placed, isolate side up, onto a bibulous support saturated with an aqueous buffer, generally of about pH 6 to 8, depending mainly on the denaturing and lysing reagent(s) employed. If, for example, a base was employed, the cell sample is placed in a neutralizing buffer of about pH 6-8 with 1.0 NaCl to remove the base. More than one such neutralizing treatment may be conducted.

In the fixation step, the single-stranded form of the nucleic acid(s) is affixed on the support by any means known in the art. One such method involves exposing the support to UV light or to a drying solvent or sufficient heat to dry the sample, preferably from about 50° to 90° C. Drying to remove liquid from the support may be accomplished, for example, by baking or by washing with ethanol.

Once the nucleic acid(s) is affixed, it can be assayed by contact with an effective amount of the hybridization probe herein under hybridization conditions. Preferably, the hybridization step is preceded by a prehybridization step wherein the affixed sample is contacted with an amount of a reagent effective to prevent nonspecific reaction of the support with the probe to be employed. In this prehybridization step the support is incubated at room temperature or at an elevated temperature with the prehybridization reagent solution and usually gentle stirring for a time sufficient to react with the support thoroughly. The reagent solution employed for this purpose preferably comprises from about 10 to 80 volume percent, more preferably about 50 volume percent, of an inert polar organic solvent. An example of a preferred prehybridization solution for this purpose is one consisting of about 25–50% formamide, 5×SSPE, (SSPE is sodium saline phosphate EDTA with the formulation provided in Maniatis et al., *Molecular Cloning: A Laboratory Manual* Cold Spring Harbor, N.Y., pub. 1982), 0.1 to 1.0% (w/v) sodium dodecyl sulfate, and about 150 µg/ml of sonicated denatured DNA. Optional components which may be present include sodium dextran sulfate of from about 100 to 1,000 kdal in an amount of about 1 to 10 weight percent, bovine serum albumin, ovalbumin, polyvinylpyrrolidone, Ficoll, 0.5 to 2% wt/vol glycine in Denhardt's solution, transfer-RNA, herring sperm DNA or other similar reagents in a citrate or phosphate buffer of pH 6–9.

After the prehybridization step the probe is added to a hybridization solution, which is essentially the same as the prehybridization solution described above, with minor variations and optionally including, e.g., 0–10% dextran sulfate. The particular hybridization solution chosen will depend mainly on the specific hybridization conditions employed, such as temperature. The amount of probe in the solution will depend on the label, the amount of probe which can be bound to the sample nucleic acid, and the hybridization conditions. Generally, excess over stoichiometric amounts of the probe relative to the sample nucleic acid is present to enhance the rate of binding of the probe to the affixed nucleic acid sequence.

Hybridization conditions may vary depending on the ultimate goal desired. The conditions of hybridization are chosen both to optimize the reannealing of the nucleic acid as well as to eliminate non-specific binding to the support matrix, affecting background. Stringency is governed by adjusting temperature, probe length, ionic strength, etc. Changing the concentration of formamide in the solution from about 20% to 50% will alter the polarity and thus the stringency of the hybridization. Generally the hybridization will occur at about 25° to 75° C., preferably 35° to 65° C., for 0.25 to 50 hours, preferably 15–24 hours, these conditions being dependent mainly on the concentration of the specific probe and nucleic acid sample employed, as well as the concentration of other ingredients in the medium. One skilled in the art of hybridization will be able to make the appropriate adjustments in conditions. The greater the stringency of the conditions, the greater the required complementarity for hybridization between the probe and the target nucleic acid.

After the hybridization step the cell, body fluid, or viral or tissue sample for the solid phase hybridization assay procedure is washed of unhybridized probe by adding to it a washing solution. Typically, the washing solution consists of sodium chloride, sodium citrate and a detergent of some type such as sodium dodecyl sulfate or Tween 20 in amounts analogous to those used for the hybridization solution. The contact time for washing varies mainly with the type of solution but generally ranges from about 5 minutes to 3 hours or more. The support on which the sample is deposited may then be rinsed at room temperature with dilute sodium citrate-sodium chloride solution before it is subjected to detection means.

The probe itself can be detected by treating it with a means by which the label moiety is capable of being detected and determining the presence of the probe using an appropriate detection technique. Detection means are those described above for the label moieties and include spectroscopic, photochemical, immunochemical, biochemical or chemical means. Immunochemical means include antibodies which are capable of forming a complex with the probe under suitable conditions, and biochemical means include polypeptides or lectins capable of forming a complex with the probe under the appropriate conditions. The antibody, polypeptide or lectin must be capable of detection or include a moiety which can be detected when the complex is formed. Examples of such includable detectable moieties include fluorescent dyes, electron dense reagents or an enzyme capable of depositing an insoluble reaction product or being detected chromogenically. Usually the antibody, polypeptide or lectin will be coupled to an enzyme which will react with a chromogenic substrate. Using an avidin-enzyme or streptavidin-enzyme complex, for example, to detect hybridized probe labeled with biotin involves washing off the unreacted avidin-enzyme or streptavidin-enzyme complex, adding a chromogenic substrate for the enzyme, and reading the resulting color change. If the enzyme is horseradish peroxidase, the substrate may be 3,3′,5,5′-tetramethylbenzidine. Detection of this substrate and other benzidines as meriquinone salts or immobilized complexes is described more fully in copending U.S. patent application Ser. No. 784,329, filed Oct. 4, 1985 entitled "Ionic Compounds Containing The Cationic Meriquinone Of A Benzidine" to W. Bloch et al., the disclosure of which is incorporated herein by reference. Proteins which become luminescent when treated appropriately may also be employed in detection of the labeled probe.

For HLA typing, the restriction fragment pattern of the unknown sample can be compared with the restriction fragment pattern of a known sample. The molecular weights of the restriction fragment can be determined by comparison to molecular weight markers.

For added sensitivity of detection, the probes herein may also be used in conjunction with a polymerase chain reaction for amplifying target nucleic acid sequences utilizing primers and nucleotides and DNA polymerase to synthesize primer extension products which are utilized as templates to produce additional target sequences. This technology is described more fully in abandoned U.S. application Ser. No. 716,975 filed Mar. 28, 1985 to K. Mullis, the disclosure of which is incorporated herein by reference. A continuation-in-part of Ser. No. 716,975 was filed on Oct. 25, 1985, as U.S. patent application Ser. No. 791,308 which issued as U.S. Pat. No. 4,683,202, on July 28, 1987.

The following examples illustrate specific embodiments of the invention, which are not intended to be limiting to any degree. In the examples the percentages and parts are given in weight units unless otherwise noted and the temperatures in degrees Celsius unless otherwise noted. Correct elemental analysis signifies a discrepancy between calculated and found values of no more than 0.4%.

EXAMPLE 1

Preparation of N-Biotinyl,N'-(4'-methylene trioxsalen)-3,6,9-trioxaundecane-1,11-diamine [Compound A (BP3)]

A. Synthesis of Bis-o,o'-Tosyl-3,6,9-Trioxa-undecane-1,11-diol (Compound I)

To a chilled solution of 42 g of tetraethylene glycol in 500 ml of dry pyridine was added 100 g of p-toluene sulfonyl chloride. The solution was stirred at 4° C. for 18 hours. To the solution was added 100 ml of methanol and stirring was continued for an additional hour. The mixture was poured into one liter of ice water. The water was decanted and the oily residue was partitioned between 300 ml of chloroform and 100 ml of water. The organic phase was washed with 0.5 N citric acid (250 ml) and brine (250 ml). The organic extract was dried over magnesium sulfate, filtered and concentrated to a residue which was adsorbed onto 25 g of silica gel and fractionated on a column using chloroform:methanol 97:3 as eluant. Fractions containing the product were pooled and concentrated to a yellow syrup.

B. Synthesis of 1,11-Diazido-3,6,9-trioxa-undecane (Compound II)

To a solution of 50.3 g of Compound I in 250 ml of dry dimethylformamide (DMF) was added 30 g of lithium azide. The mixture was heated to 80° C. with stirring until TLC on silica gel (chloroform:methanol 97:3) revealed no starting material remaining. The solvent was removed under vacuum and the residue partitioned between 500 ml of ether and 250 ml of brine. The ether layer was dried over magnesium sulfate, filtered and concentrated to an oil.

C. Synthesis of 1,11-Diamino-3,6,9-trioxa-undecane (Compound III)

To a chilled, stirred solution of 24.4 g of Compound II in 250 ml pyridine was added 89 g of triphenyl phosphine. Nitrogen bubbles evolved. The solution was stirred with ice cooling for 45 minutes and then allowed to warm to room temperature. After 45 minutes at room temperature 100 ml of concentrated ammonium hydroxide was added and the mixture stirred overnight. The mixture was partitioned between 500 ml of 0.5N citric acid and 250 ml of ether. The aqueous phase was washed with ether (2×250 ml) to remove triphenyl phosphine oxide. The aqueous phase was saturated with sodium chloride and extracted with 1-butanol (4×250 ml) and dichloromethane (4×250 ml). The combined alcohol and dichloromethane extracts were concentrated under reduced pressure and the residue was taken up in 100 ml of ethanol. Concentrated hydrochloric acid (15 ml) was added and the solvent removed under reduced pressure. The residue was crystallized from ethanol/ether. The hygroscopic crystals were dried under vacuum.

D. Synthesis of N-Tert-butyloxycarbonyl-3,6,9-trioxaundecane (Compound IV)

To a solution of 13.26 g of Compound III and 8 ml of triethylamine in 100 ml of methanol was added a solution of 12 g of di-tert-butyl dicarbonate in 10 ml of methanol. Carbon dioxide bubbles evolved and the reaction mixture was slightly exothermic. Stirring was continued until gas evolution ceased. The solvent was removed under reduced pressure and the residue adsorbed onto 20 g of silica gel and fractionated on a column using dichloromethane:methanol:acetic acid, 70:30:5, as eluant. The fractions containing product were pooled and concentrated to yield the mono-BOC (butyloxycarbonyl) derivative as a syrup.

E. Synthesis of N-(tert-Butyloxycarbonyl),N'-(4'-methylene trioxsalen)-3,6,9-trioxa-undecane (Compound V)

To a solution of 280 mg of Compound IV and 120 mg of triethylamine in 4 ml of dry toluene was added 224 mg of chloromethyl trioxsalen. The mixture was heated at 110° C. overnight in the dark. TLC on silica gel using as eluant chloroform:methanol 8:1 showed no starting material remaining. The reaction mixture was adsorbed onto 5 g of silica gel and fractionated on a column using chloroform:methanol 8:1 as eluant. Fractions containing the product (fluorescent and ninhydrin positive) were pooled and concentrated to a syrup which spontaneously crystallized.

F. Synthesis of N-Biotinyl,N'-(4'-methylene trioxsalen)-3,6,9-trioxa-undecane-1,11-diamine (Compound A)

A solution of 600 µmole of Compound V in 5 ml of 97% formic acid sat overnight at room temperature. This quantitatively removed the BOC protecting group. The solvent was removed under reduced pressure and the residual amine used without further purification. A solution of this amine in dry DMF (2.86 µmole in 25 µl) and 10 µl of a 1M solution of triethylamine in dry DMF was added to 1 mg of the N-hydroxysuccinimide ester of biotin. The solution sat in the dark for two hours at room temperature and was purified by preparative TLC on silica gel using as eluant chloroform:methanol 4:1. The low Rf product band which was fluorescent and contained biotin was scraped and washed with 1 ml methanol to elute the product, Compound A.

EXAMPLE 2

Preparation of 1-(Biotinylamino)-13-(4,5',8-trimethylpsoralen-4'-yl)-3,6,9,12-tetraoxa-tridecane [Compound B (BP6)]

A. Synthesis of Mono-toluenesulfonyl Tetraethylene Glycol (Compound VI)

To a solution of tetraethylene glycol (42 g; 216 mmole) in 500 ml of dry pyridine cooled to 4° C. was added p-toluene sulfonyl chloride (50 g; 262 mmole). The solution was stirred in the cold overnight. The pyridine was evaporated and ca. 300 ml of tolune was used to azeotrope the pyridine. The residue was taken up in 60 ml of methanol and 30 g of silica gel was added. The solvent was removed under reduced pressure and the residue fractionated on a silica gel column using 97:3 chloroform:methanol as eluant. The mono-tosylate obtained was used directly for the next reaction.

B. Synthesis of 11-Azido-3,6,9-trioxa-undecanol (Compound VII)

Compound VI was dissolved in 250 ml of dry dimethylformamide, and lithium azide (15 g; 306 mmole) was added. The mixture was stirred and heated to 80°–100° C. After several hours, thin layer chromatography (TLC) using 97:3 chloroform:methanol on silica gel showed all ultraviolet-absorbing material at the origin (lithium tosylate). The solvent was removed under reduced pressure and the residue was taken up in tetrahydrofuran, and 40 g of silica gel was added. The solvent was removed and the residue fractionated on a silica gel column using ethyl acetate as eluant. Fractions containing the product were pooled and concentrated. Correct elemental analyses were obtained for carbon, hydrogen and nitrogen. On TLC, the Rf of the product band on silica gel using ethyl acetate was 0.21.

C. Synthesis of 11-Amino-3,6,9-trioxa-undecanol (Compound VIII)

To a solution of Compound VII (15.94 g; 72.7 mmole) in 100 ml of pyridine was added triphenylphosphine (29 g; 111 mole). After stirring for one hour, at which time gas evolution had subsided, 50 ml of concentrated aqueous ammonium hydroxide was added and the mixture stirred overnight. The reaction mixture was concentrated under vacuum and the residue partitioned between 200 ml of water and 200 ml of ether (aqueous layer at pH 2). The aqueous layer was washed twice with 200 ml ether each time. The aqueous layer was adjusted to pH 11 with solid sodium hydroxide and extracted three times with 150 ml n-butanol each time. The butanol extract was dried over sodium sulfate, filtered and concentrated. The residue was taken up in tetrahydrofuran and filtered. The filtrate was evaporated to a syrup which was azeotroped with toluene.

D. Synthesis of 11-tert-Butyloxycarbonylamino-3,6,9-trioxaundecanol (Compound IX)

To a suspension of Compound VIII (12 g; 62.1 mmole) in 100 ml of dry tetrahydrofuran was added di-tert-butyl dicarbonate (15 g; 68.7 mmole). Much gas was generated. Triethylamine (10 ml; 7.26 g; 71.3 mmole) was added and the mixture stirred at room temperature. When gas evolution ceased, the solution was diluted with methanol and 20 g of silica gel was added. The solvents were removed under reduced pressure and the residue was fractionated on a column of silica gel using 8:1 chloroform:methanol as eluant. Fractions containing the product were pooled and concentrated to a syrup. Correct elemental analyses were obtained for carbon, hydrogen and nitrogen.

E. Synthesis of 1-(tert-Butyloxycarbonylamino)-13-(4,5',8-trimethylpsoralen-4'-yl)-3,6,9,12-tetraoxa-tridecane (Compound X)

Chloromethyltrioxsalen (277 mg; 1 mmole) and lithium iodide (135 mg; 1.01 mmole) were mixed in 10 ml of dry tetrahydrofuran. The mixture was sonicated briefly. To the mixture was added Compound IX (293 mg; 1 mmole). A clear, yellow solution resulted. To the solution was added potassium tert-butoxide (115 mg; 1.03 mmole). A precipitate formed and the mixture was stirred in the dark and refluxed gently for several hours. The reaction was diluted with 2 ml of tetrahydrofuran, the suspension was centrifuged, and the supernatant was filtered through a 0.45 micron syringe filter. The filtrate was neutralized by the addition of three drops of glacial acetic acid. The solvent was removed under reduced pressure and the residue reconstituted in 2 ml of methanol. The solution was applied to four 20 cm×20 cm preparative silica gel plates. The plates were developed in ethyl acetate and the product bands were scraped from the plates and eluted into ca. 50 ml of methanol. The methanol extract was filtered and concentrated to dryness, reconstituted in 10 ml of methanol, and filtered by syringe through a 0.45 micron filter. A 7.96M solution was obtained which was used for further reactions. Correct elemental analysis for carbon, hydrogen and nitrogen was obtained. The Rf is 0.27 (silica gel; ethyl acetate).

F. Synthesis of 1-(Biotinylamino)-13-(4,5',8-trimethylpsoralen-4'-yl)-3,6,9,12-tetraoxa-tridecane (Compound B)

Compound X (15.4 mg; 28.9 μmoles) was taken up in 1 ml of 2 M trifluoroacetic acid in acetonitrile and allowed to sit at room temperature in the dark until thin layer chromatography using ethyl acetate on silica gel showed no starting material remaining. The solution was evaporated under reduced pressure and the residue dissolved in 100 μl of dry pyridine. To this solution was added biotin N-hydroxysuccinimide ester (NHS-biotin) (10 mg; 29.4 μmole). The mixture sat at room temperature in the dark for three days and was then taken to dryness and the residue dissolved in 500 μl of methanol. The mixture was centrifuged to remove a small amount of insoluble material. The supernatant was applied to a 20 cm×20 cm preparative layer silica gel plate, and the plate was developed with 90:10:5 dichloromethane:methanol:acetic acid. The product band was removed from the plate and eluted with methanol. The extract was filtered and taken to dryness. The residual material was submitted for high resolution mass spectral analysis. Found: Molecular weight=682.2781 ($C_{33}H_{45}N_3O_9S$+Na).

The Rf product band eluted at 0.33 (silica gel; 90:10:5 dichloromethane:methanol:acetic acid).

EXAMPLE 3

Preparation of Probes and Hybridization on Genomic Southern Blots

I. Biotinylation of DNA Using Compounds A (BP3) and B (BP6)

A probe for typing the human leukocyte antigen (HLA) system, designated as an HLA-DPα M13 hybridization probe, was prepared as follows:

A. Preparation of HLA-DRα Probe for Screening cDNA Library

An HLA-DRα probe was made to screen a cDNA library to identify a HLA-DPα clone as follows.

Four 11-mer oligonucleotides were prepared based on the known NH2-terminal amino acid sequence (Glu, Phe, Tyr, Leu) of positions 11–14 of HLA-DRα antigen. The base sequences for the four oligonucleotides were as follows: (1) AGGTAAAATTC, (2) AGGTAGAATTC, (3) AGGTAAAACTC, and (4) AGGTAGAACTC. These sequences are all complementary to the codons for the indicated peptide sequence and were chosen to minimize degeneracy. The ambiguities are located at sequences positions 2, 3, 6, and 9. A G at positions 2 and 3 was chosen to minimize the destabilizing effect of potential mismatched bases (G is capable of forming a wobble pair with U).

Because the four oligonucleotides were complementary to codons for amino acids 11–14, oligonucleotide primed cDNA synthesis on HLA-DRα mRNA was expected to generate a product of about 150–200 nucleotides. This estimate was based on a leader sequence of 75 nucleotides and assumes a 5' untranslated region of 75–125 nucleotides.

The specificities of the four 11-mers were compared by using them individually as primers in cDNA synthesis reactions using membrane-bound B cell mRNA, free B cell mRNA, and T cell mRNA as template. Only the AGGTAGAACTC oligonucleotide primed a cDNA band of 175 nucleotides which was enriched in reactions on B cell membrane-bound mRNA template. The specificity of this 11-mer oligonucleotide was confirmed by extending the primer in a cDNA synthesis reaction in the presence of a single dideoxy triphosphate and three deoxy triphosphates, an approach which has proved successful in the isolation of the HLA-B7 cDNA clone (Sood, et al, PNAS (1981) 78:616620). In the presence of dideoxy dATP, a minor cDNA band corresponding to a predicted 18-nucleotide primer extension product was observed. The additional seven nucleotides were determined by the wandering spot sequencing technique to be GGCCTGA. The following two additional nucleotides, AT, were inferred from the Ile codon, giving a nine nucleotide sequence that corresponded to the HLA-DRα antigen amino acids at positions 8, 9, and 10.

A 20-nucleotide fragment having the above determined sequence (AGGTAGAACTCGGCCTGAAT) was then synthesized by the triester method. The specificity of the 20-mer as a primer was examined in a cDNA synthesis reaction on poly(A+) mRNA from a B cell line. A major cDNA band, 175 nucleotides long, was synthesized; the nucleotide sequence of the eluted band corresponded to the expected sequence for HLA-DRα.

The specificity of the 20-nucleotide fragment as a hybridization probe was analyzed on a Northern blot of poly(A+) mRNA. A unique band, at 1200–1300 nucleotides, resulted from probing B cell mRNA, but not T cell mRNA, with the $^{32}$P-labeled 20-mer nucleotide probe. Membrane-bound mRNA was enriched for the mRNA which hybridized to the 20-nucleotide probe.

An HLA-DRα cDNA clone was identified in a cDNA library with the above described 20-mer probe as follows. Membrane-bound RNA and free RNA were prepared, using phenol-chloroform extraction in the presence of Vanadyl complexes, from the human lymphoblastoid B cell line, CA. Poly(A+) mRNA, isolated by affinity chromatography with Poly U-Sepharose, was translated in an in vitro rabbit reticulocyte system. The partition of specific mRNA's into the membrane-bound and free fractions was monitored by 2D gel analysis of the $^{35}$S-labeled products of in vitro translation. A double-stranded cDNA library was prepared from the membrane-bound mRNA using reverse transcriptase, DNA Polymerase I, and Sl nuclease. Following tailing with dCTP using terminal transferase, the cDNA was inserted and ligated to preparations of the plasmid pBR322 which had been digested with Pst and tailed with dGTP.

Initial screening of the library was carried out as follows. Duplicate sets (~4,000 clones/set) of Grunstein-Hogness colony filters were prepared. One set was probed with $^{32}$P cDNA made from size fractionated mRNA from the B cell line, CA. Sucrose gradient fractions were translated in an in vitro rabbit reticulocyte system and the $^{35}$S-labeled products analyzed by 2D gel electrophoresis to determine the appropriate fractions. The other set of filters was probed with $^{32}$P cDNA made from mRNA from the T cell line, Molt-4. A subset of about 150 clones, derived from membrane-bound, B cell specific, 12–14s mRNA, was defined by this initial screening.

Plasmid DNA was prepared from 25 pools, each consisting of 5 candidate cDNA clones and analyzed by dot hybridization with the $^{32}$P-labeled 20-nucleotide probe. Pool 14 plasmid DNA hybridized specifically with the probe. Subsequently, the individual members of the pool were tested; cDNA sequences complementary to the hybridization probe were restricted to the clone identified as 18C7.

In Northern blots, the $^{32}$P-labeled 18C7 nick translated probe hybridizes to a B cell mRNA of the same length (about 1200 to about 1300 nucleotides) as the band complementary to the 20-nucleotide probe. In genomic blots with DNA from a hamster-human hybrid containing the human chromosomes 6 and 3, the 18C7 probe hybridizes to a unique restriction fragment absent in the hamster parent, mapping the 18C7 DNA sequences to chromosome 6.

A more precise mapping was possible using the cell line 6.3.6 which has a small deletion at a defined site on the short arm of one homologue of the chromosome 6 pair. This deletion variant fails to express the HLA-A, B, C and HLA-DR specificities associated with one chromosome 6 halotype. In genomic blots 18C7 hybridizes to two restriction fragments from the parent cell line, presumably from the two chromosome 6's. Only one fragment is observed in DNA from the deletion variant; the other fragment is presumably derived from the chromosome which has been deleted. This result maps DNA sequences complementary to the 18C7 clone to the chromosomal site defined by the 6.3.6 deletion.

The human HLA-D locus is homologous to the mouse I region. In genomic blots with DNA from mouse congenic lines, inbred lines which differ only at the I region, the 18C7 probe hybridized to a restriction fragment that was different with each congenic line. This result maps DNA sequences complementary to the 18C7 probe hybridized to a restriction maps DNA sequences complementary to the 18C7 clone to the mouse region and therefore to the human HLA-D locus.

The 18C7 clone was confirmed as being HLA-DRα by analyzing its DNA sequence by the Maxam-Gilbert technique (Methods in Enzymology (1980) 65:499–560) using the endonucleases PstI, HinfI, TaqI, Sau3A, AvaII, and BglI. The sequence for the coding strand of the HLA-DRα clone is given below.

| ATCATAGCTG | TGCTGATGAG | CGCTCAGGAA | TCATGGGCTA | TCAAAGAAGA |
|---|---|---|---|---|
| ACATGTGATC | ATCCAGGCCG | AGTTCTATCT | GAATCCTGAC | CAATCAGGCG |
| AGTTTATGTT | TGACTTTGAT | GGTGATGAGA | TTTTCCATGT | GGATATGGCA |
| AAGAAGGAGA | CGGTCTGGCG | GCTTGAAGAA | TTTGGACGAT | TTGCCAGCTT |
| TGAGGCTCAA | GGTGCATTGG | CCAACATAGC | TGTGGACAAA | GCCAACCTGG |
| AAATCATGAC | AAAGCGCTCC | AACTATACTC | CGATCACCAA | TGTACCTCCA |
| GAGGTAACTG | TGCTCACGAA | CAGCCCTGTG | GAACTGAGAG | AGCCCAACGT |
| CCTCATCTGT | TTCATCGACA | AGTTCACCCC | ACCAGTGGTC | AATGTCACGT |
| GGCTTCGAAA | TGGAAAACCT | GTCACCACAG | GAGTGTCAGA | GACAGTCTTC |
| CTGCCCAGGG | AAGACCACCT | TTTCCGCAAG | TTCCACTATC | TCCCCTTCCT |

-continued

| | | | | |
|---|---|---|---|---|
| GCCCTCAACT | GAGGACGTTT | ACGACTGCAG | GGTGGAGCAC | TGAGGCTTGG |
| ATGAGCCTCT | TCTCAAGCAC | TGGGAGTTTG | ATGCTCCAAG | CCCTCTCCCA |
| GAGACTACAG | AGAACGTGGT | GTGTGCCCTG | GGCCTGACTG | TGGGTCTGGT |
| GGGCATCATT | ATTGGGACCA | TCTTCATCAT | CAAGGGAGTG | CGCAAAAGCA |
| ATGCAGCAGA | ACGCAGGGGG | CCTCTGTAAG | GCACATGGAG | GTGATGATGT |
| TTCTTAGAGA | GAAGATCACT | GAAGAAACTT | CTGCTTTAAT | GACTTTACAA |
| AGCTGGCAAT | ATTACAATCC | TTGACCTCAG | TGAAAGCAGT | CATCTTCAGC |
| GTTTTCCAGC | CCTATAGCCA | CCCCAAGTGT | GGTTATGCCT | CCTCGATTGC |
| TCCGTACTCT | AACATCTAGC | TGGCTTCCCT | GTCTATTGCC | TTTTCCTGTA |
| TCTATTTTCC | TCTATTTCCT | ATCATTTTAT | TATCACCATG | CAATGCCTCT |
| GGAATAAAAC | ATACAGGAGT | CTGTCTCTGC | TATGGAATGC | CCCATGGGGC |
| TCTCTTGTGT | ACTTATTGTT | TAAGGTTTCC | TCAAACTGTG | ATTTTTCTG |

A $^{32}$P-labeled HLA-DRα probe was made from the clone by nick translation.

B. Preparation of Hybridization Probes for HLA-DPα (Using Clones p29G8 and pDA318)

A HLA-DPα clone, p29G8, was identified by screening the cDNA library described above with the nick-translated HLA-DRα probe under hybridization conditions of reduced stringency to allow detection of related but distinct DNA sequences. The hybridization conditions were as follows.

Hybridize in 50% formamide, 5×SSPE (1×SSPE=0.18M NaCl, 10 mM NaH$_2$PO$_4$, 1 mM Na$_2$EDTA, pH 7.0), 0.1% sodium dodecyl sulfate (SDS), 5×Denhardt's (5×Denhardt's=0.1% w/v each bovine serum albumin, Ficoll, polyvinyl pyrollidone), 200 μg/ml sheared denatured salmon sperm DNA, at 37° C. for 24 hours with 1×10$^6$ cpm $^{32}$P-labeled HLA-DRα probe (2×10$^8$ cpm/μg, labeled by nick translation). Wash filters 3×15 minutes at room temperature in 5×SSPE, 0.1% SDS.

Under conditions of high stringency (wash at 0.1×SSPE, 65° C.), p29G8 hybridizes strongly only to itself. The coding strand of the p29G8 clone was sequenced using the Maxam-Gilbert procedure.

In genomic Southern blots, the p29G8 probe hybridizes to genomic restriction fragments distinct from those which hybridize to the HLA-DRα probe in DNA from an HLA hemizygous cell line (6.3.6). The genomic blot pattern with DNA from the cell line T5-1 and its HLA hemizygous derivative 6.3.6 indicates that the p29G8 locus maps within the HLA region. Comparison of the amino acid sequence encoded by this clone with published amino acid sequence data for HLA-DPα antigen indicated that p29GB is an HLA-DPα clone. A $^{32}$P-labeled probe was made from the clone by nick translation.

The p29G8 probe was hybridized to another cDNA library made with EcoRI linking. The DP-α cDNA sequence was subcloned into the EcoRI site of pBR328, which is commercially available from Boehringer-EcoRI Mannheim, and is a relative of pBR322, to produce the plasmid, pDA318, which was deposited in an MM294 host with the American Type Culture Collection under accession No. 39,917 on Nov. 8, 1984. The plasmid pDA318 is larger than p29G8 and includes the p29G8 sequence. The sequence of the cDNA insert in pDA318 is given below.

```
AGTCTCATCTGCCTCCACTCGGCCTCAGTTCCTCATCACTGTTCCTGTGCTCACAGTCAT
CAATTATAGACCCCACAACATGCGCCCTGAAGACAGAATGTTCCATATCAGAGCTGTGAT
CTTGAGAGCCCTCTCCTTGGCTTTCCTGCTGAGTCTCCGAGGAGCTGGGGCCATCAAGGC
GGACCATGTGTCAACTTATGCCGCGTTTGTACAGACGCATAGACCAACAGGGGAGTTTAT
GTTTGAATTTGATGAAGATGAGATGTTCTATGTGGATCTGGACAAGAAGGAGACCGTCTG
GCATCTGGAGGAGTTTGGCCAAGCCTTTTCCTTTGAGGCTCAGGGCGGGCTGGCTAACAT
TGCTATATTGAACAACAACTTGAATACCTTGATCCAGCGTTCCAACCACACTCAGGCCAC
CAACGATCCCCCTGAGGTGACCGTGTTTCCCAAGGAGCCTGTGGAGCTGGGGCCAGCCCAA
CACCCTCATCTGCCACATTGACAAGTCCTTCCCACCAGTGCTCAACGTCACGTGGCTGTG
CAACGGGGAGCTGGTCACTGAGGGTGTCGCTGAGAGCCTCTTCCTGCCCAGAACAGATTA
CAGCTTCCACAAGTTCCATTACCTGACCTTTGTGCCCTCAGCAGAGGACTTCTATGACTG
CAGGGTGGAGCACTGGGGCTTGGACCAGCCGCTCCTCAAGCACTGGGAGGCCCAAGAGCC
AATCCAGACGCCTGAGACAACGGAGACTGTGCTCTGTGCCCTGGGCCTGGTGCTGGGCCT
AGTCGGCATCATCGTGGGCACCGTCCTCATCATAAAGTCTCTGCGTTCTGGCCATGACCC
CCGGGCCCAGGGGACCCTGTGAAATATCTGTAAAGGTGACAAAATATCTGAACAGAAGAGG
ACTTAGGAGAGATCTGAACCAGCTGCCCTACAAACTCCATCTCAGCTTTTCTTCTCACTT
CATGTGAAAACTACTCCAGTGGCTGACTGAATTGCTGACCCTTCAAGCTCTGTCCTTATC
CATTACCTCAAAGCAGTCATTCCTTAGTAAAGTTTCCAACAAATAGAAATTAATGACACT
TTGGTAGCACTAATATGGAGATTATCCTTTCATTGAGCCTTTTATCCTCTGTTCTCCTTT
GAAGAGCCCCTCACTGTCACCTTCCCGAGAATACCCTAAGACCAATAAATACTTCAGTAT
T
```

Figure 2:
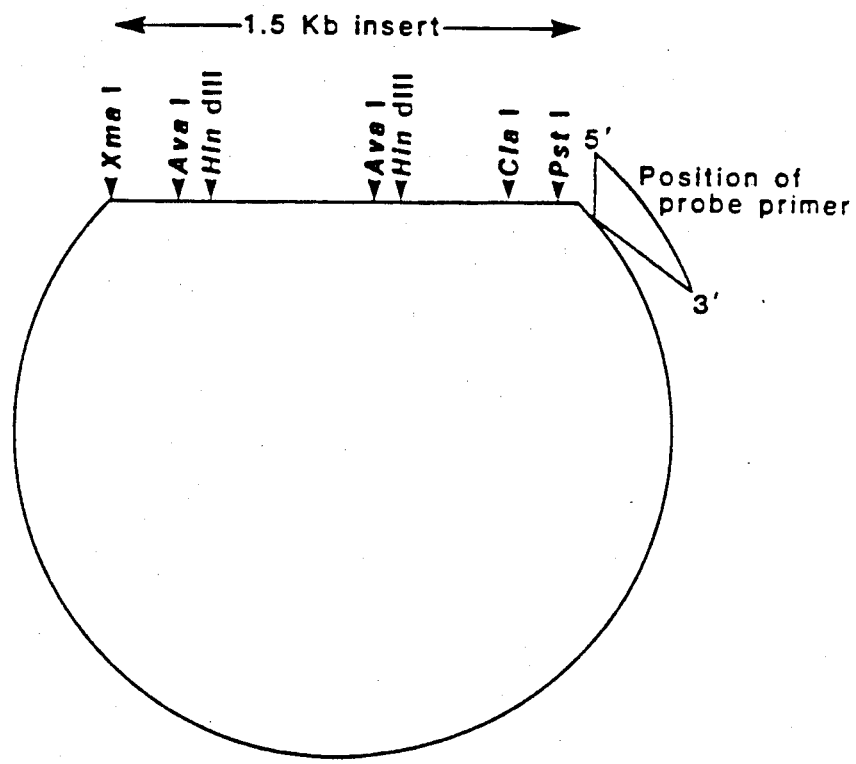
FIG. 2 represents a restriction map of M13mp9CHL2.1 containing the insert from the plasmid pCHL2.

FIG. 1 shows a restriction map of the 7 kilobase Chlamyhdia trachomatis clone pCHL2 (publicly available plasmid) insert subcloned in the BamHI site of pBR 322. The map shows the origin of subclone M13mp9CHL2.1, which has an inert of 1500 base pairs. This 1.5 kilobase pair fragment, between the PstI and XmaI sites, was cut out with the enzymes PstI and XmaI and ligated into the PstI and XmaI sites in M13mp9 to yield the subclone M13mp9CHL2.1, shown as a restriction map in FIG. 2.

The phage strain M13mp10 (commercially available from Boehringer-Mannheim and described on pages 88–89 of the 1983 BRL Catalog) was employed. The M13mp10 is essentially the same as M13mp9 except for its cloning region, which is provided in FIG. 3B. FIG. provides the differences between these regions of M13mp9 and M13mp10. Both the cDNA insert of pDA318 and M13mp10 R.F. DNA were cut with EcoRI restriction enzyme and then the DNA fragments were ligated together and used to transform the E. coli strain JM103, which is publicly available from Bethesda Research Laboratories in Bethesda, Md. The procedure followed for preparing the transformed strain is described in Messing, J. (1981) *Third Cleveland Symposium on Macromolecules: Recombinant DNA*, Ed. A. Walton, Elsevier, Amsterdam, 143-153. Restriction analysis established that one of the single-stranded M13 candidates excreted into the medium contained the desired pDA318 1200 base insert in the desired orientation. M13 phage containing the 1200 base insert were isolated and the DNA was extracted and purified.

This single-stranded M13 phage DNA was labeled separately with Compound A (BP3) or Compound B (BP6) by combining 100 μg/ml of the probe with 30 μM of Compound A or 300 μM of Compound B. The tubes were irradiated with ultraviolet light at 360 nm at 30 mW/cm$^2$ for 10 minutes and the reacted materials were isolated by ethanol precipitation. (More generally for incorporation, the concentration of probe may range from 100 μg/ml to 1 mg/ml.)

Biotinylated molecular weight markers for identifying the bands seen on Southern blots were made from bacteriophage Lambda DNA which had been digested to completion with the restriction endonuclease, BstEII (supplied by New England Biolabs), and biotinylated in the manner just described for labeling a DNA probe.

II. Extent of Incorporation of Label

The extent of incorporation of the biotin labeled into each probe was determined by measuring the incorporation of a tritium-labeled biotinylated psoralen. To measure incorporation, Compound A containing tritium was complexed and reacted with DNA. After the irradiation step, the entire reaction mixture was placed in 0.3M sodium acetate. Two volumes of ethanol were added, and then the mixture was chilled in a dry ice/ethanol bath. The precipitated material was centrifuged at about 10,000×g for 15 minutes to pellet it. Next, the supernatant was discarded and the pellet was washed with −20° C. 80% ethanol. The pellet was resuspended in 10 mM Tris-HCl, 1 mM EDTA, pH 8.0. For determining the DNA concentration, the optical density was measured at 260 nm. To measure the amount of Compound A which had been incorporated, a small aliquot of the labeled material was counted by scintillation spectroscopy.

III. Hybridization of Probes to HLA Insert

Two μg of human DNA were digested with the restriction endonuclease BglII, electrophoresed through 1% agarose minigels, and transferred to one of three nylon membranes (Genatran 45 of Plasco Inc., Zeta-Probe of BioRad, or Nytran of Schleicher and Schuell), using the method as described by Southern ((1975) *JMB* 98:503–517). In some lanes biotinylated DNA molecular weight markers (described above) and/or a positive control consisting of genomic DNA isolated from a homozygous typing cell line WT51 (Tissue Antigen Laboratory, Imperial Cancer Research Fund, London, England) digested with the same restriction endonuclease was included. After transfer to the membrane the filter-bound human DNA was fixed on the membrane using the standard procedure with base, neutralization with Tris-HCl buffer and baking for one hour or longer at 80° C. in a vacuum oven, as described by Southern, supra. The membrane was then wetted with distilled water for one minute, and placed in a sealable pouch. A prehybridization solution was then added to the membrane consisting of 5×Denhardt's solution with 50% formamide, 5×SSPE, 0.5% (w/v) SDS, 0–10% (preferably 5%) dextran sulfate, and 150 μg/ml denatured herring sperm DNA (available from Sigma). The membrane was incubated with the solution for 2–4 hours at 42° C. Then a hybridization solution was added to the membrane in an amount of 0.1 ml solution/cm$^2$ membrane consisting of 5×Denhardt's solution with 50% formamide, 5×SSPE, 0.5% (w/v) SDS, 0–10% dextran sulfate, 150 μg/ml denatured herring sperm DNA, and 50–200 ng per ml of either probe and the membrane was incubated overnight (about 14–18 hours) at 42° C. The membrane was then washed three times for five minutes each with shaking at room temperature in 2×SSPE, 0.5% Tween 20 and three times at 60° C. for five minutes with shaking in 0.2–0.3×SSPE, 0.5% Tween 20 to produce a probe-hybridized Southern blot.

IV. Horseradish Peroxidase-Streptavidin (HRP-SA) Conjugate Preparation

Horseradish peroxidase (HRP) quantities were calculated from an assumed molecular weight of 40,000 g/mole and an assumed $A_{402}$, 1 cm, 0.1% of 2.5. Streptavidin (SA) quantities were calculated from an assumed molecular weight of 60,000 g/mole and an assumed $A_{280}$, 1 cm, 0.1% of 3.0.

To 40 mg of HRP (Sigma Chemical Co. Type VI), dissolved in 1.9 ml of 0.10M Na phosphate, pH 7.5, and dialyzed at 4° C. against the same buffer, were added 0.14 ml of 14 mg/ml mal-sac-HNSA ester dissolved in the same buffer. [mal-sac-HNSA ester is the subject of copending patent application Serial No. 637,905 filed Aug. 6, 1984 and is also described by Bhatnagar et al., *Peptides:Synthesis-Structure-Function*, ed. by D. Rich et al. (Rockford:Pierce Chemical Company, 1981), p. 97 where the preparation of mal-sac-HNSA ester parallels that of DNP-SAC and TNP-SAC esters using as the acid N-maleimido-6-aminocaproic acid.]This mixture was incubated for 105 min at room temperature, desalted on a 9 ml column of Sephadex G-25 equilibrated with 0.010M Na phosphate, 0.005M EDTA, pH 6.0, and dialyzed at 4° C. against three 200 ml volumes of the same buffer. The maleimide content of the derivatized HRP was assayed by diluting 0.2 mg in 0.50 ml 0.10M Na phosphate, 0.005M EDTA, ph 7.0, adding 20 μl of 0.74 mM cysteine, incubating 5 min at room temperature, adding 33 μl of 4 mg/ml 5,5'-dithiobis(2-nitrobenzoic acid), incubating 2 min at room temperature, and measuring $A_{412}$ in a spectrophotometer. The difference in $\Delta A_{412}$ between this reaction and one for a control mixture to which no protein had been added, divided by the $\Delta \epsilon_{412}$ of $1.36 \times 10^4$ M$^{-1}$ cm$^{-1}$, gave the molarity of maleimide in the diluted HRP.

Fifteen mg of SA (Sigma Chemical Co.) were dissolved in 1.5 ml of 0.10M Na phosphate, pH 8.0, dialyzed at 4° C. against three 200 ml volumes of the same buffer, and diluted to a concentration of 6 mg/ml in the same buffer. S-acetyl mercaptosuccinic acid (SAMCA, Aldrich Chemical Co.) was dissolved in dimethyl formamide at a concentration of 8.8 mg/ml. To 12 mg of dialyzed SA were added 125 μl of this SAMCA solution with gentle stirring at room temperature over about 1 min. After 30 min incubation at room temperature, the reaction mixture was desalted on a 9 ml column of Sephadex G-25 equilibrated with 0.10M TrisCl, 0.005M EDTA, pH 6.8. The pooled protein was dialyzed at 4° C. against three 200 ml volumes of the same buffer. The dialyzed derivatized SA was concentrated at room temperature to 10 mg/ml in an Amicon 8 MC ultrafiltration device with a YM10 membrane. Ten mg of concentrated SA were mixed with 0.5 ml of 1.0M hydroxylamine in 0.10M TrisCl, 0.005M EDTA, pH 6.8 with gentle stirring. After a 30 min incubation at room temperature, the SA was desalted on a 9 ml column of Sephadex G-25 equilibrated with 0.010M Na phosphate, 0.005M EDTA, pH 6.0. A small aliquot of the pooled protein peak was assayed for reactive thiols by measuring the change in $A_{412}$ after adding 5,5'-dithiobis(2-nitrobenzoic acid) to a concentration of 1 mM in 0.10M Na phosphate, pH 8.0.

The assays of maleimide on HRP and of thiols on SA were done immediately before mixing them to perform the coupling reaction. Then 3.95 ml of 13.0 mg/ml HRP bearing 0.67 maleimides/HRP were mixed in an ice bath with 2.47 ml of 4.19 mg/ml SA bearing 9.66 thiols/SA. After a 24 hr incubation at 5 C, the unreacted thiols were blocked by adding 0.47 ml of 4.6 mg/ml N-ethyl maleimide dissolved in acetonitrile and incubating at room temperature for 30 min.

The reaction mixture was fractionated into conjugate pools of different mean HRP/SA molar ratio, separated from unreacted HRP by gel filtration chromatography on a 2.5×80 cm column of Ultrogel AcA 44 (LKB Instruments) at 4 C in 0.10M Na phosphate, pH 6.8, at a flow rate of 3 cm/hr. The composition of the conjugate pools was estimated spectrophotometrically from the $A_{402}/A_{280}$ ratio and quantitated accurately by densitometric scanning of a Nuclear Fast Green stained 6–20% gradient SDS-PAGE gel, run under reducing conditions. Approximately 10 mg of mixed 2-mer and 3-mer (species containing 2 HRP:SA and 3 HRP:SA) and 5 mg of fairly pure 1-mer were recovered from gel filtration. These conjugate pools, containing no detectable uncoupled SA or HRP, were stored at 4° C. for many months with negligible loss of protein or HRP catalytic activity. The mixture of 2-mer and 3-mer was used preferentially in detecting biotinylated DNA probe hybridized to human genomic Southern blots, but 1-mer gave almost the same intensity of staining.

V. Probe Detection

All operations took place at room temperature. The probe-hybridized Southern blot from Section III of this example was rinsed once in 35 ml of phosphate-buffered saline (2.7 mM KCl, 136.9 mM NaCl, 1.5 mM $KH_2PO_4$ and 8 mM $Na_2HPO_4$) to which had been added 0.1M NaCl and 5% Triton X-100 (Buffer A). After 5 min of gentle agitation, the rinse solvent was replaced with Buffer A containing HRP-SA at a concentration such that the component HRP was present at 0.3 μg/ml. The amount of Buffer A plus HRP-SA was 0.5–1 ml/cm² of membrane. Conjugate was incubated with the membrane for 20 min with or without agitation. Then the membrane was removed to a clean Petri dish and rinsed 5 times with 45 ml volumes of Buffer A to which had been added 0.15M 1,1-diethylurea. This was followed by one 5 minute wash with gentle agitation in 0.10M Na citrate, 5% ethanol, pH 5.0, (Buffer C) containing 0.1 mg/ml TMB. At this point, the membrane was incubated undisturbed in 50 ml of Buffer C containing 0.1 mg/ml TMB and 0.0007% $H_2O_2$. Over 15–60 minutes, dark blue bands developed on the membrane wherever biotinylated DNA was located—either biotinylated λDNA fragments used as molecular weight standards or biotinylated probe hybridized to targeted DNA. When satisfactory contrast was obtained, the substrate solution was drained from the membrane, which was rinsed four times for five minutes each with 50 ml water with gentle agitation. The washed membrane was stored in water in a sealed test tube or plastic bag in the dark at room temperature, 4° C. or −20° C.

The results indicate that both single-stranded probes adequately detected the single copy gene target, although the background was higher than when the partially double-stranded probe described in copending U.S. patent application Ser. No. 791,332 filed Oct. 25, 1985 was employed. In addition, Compound B was found to be less sensitive to the same hybridization conditions than Compound A.

It is noted that the M13 method for obtaining single-stranded nucleic acids with a single-stranded hybridization region does not involve the use of relatively expensive enzymes such as DNA polymerase I which are required in the methods of incorporating biotin into DNA taught by, e.g., Leary et al., supra, and EP No. 0,063,879 to Ward, supra. In addition, it does not require construction of a gapped circle as in the case when partially double-stranded probes are psoralenated as described in the above-identified copending application. The probes herein are particularly useful for research, e.g., in screening lambda libraries for cDNA because the technique is both fast to run and fast to detect.

The deposit identified as the plasmid pDA318 in a MM294 host was deposited with the American Type Culture Collection (ATCC) of Rockville, MD 20852 U.S.A. under accession no. 39,917 on Nov. 8, 1984 pursuant to a contract between the ATCC and the assignee of this patent application, Cetus Corporation. The contract with ATCC provides for permanent availability of the progeny of this plasmid-containing host to the public on the issuance of the U.S. patent describing and identifying the deposit or the publications or upon the laying open to the public of any U.S. or foreign patent application, whichever comes first, and for availability of the progeny of this host to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the host on deposit should die or be lost or destroyed when cultivated under suitable conditions, it will be promptly replaced on notification with a viable culture of the same host.

In summary, the present invention is seen to provide a detectable probe which may be used in hybridization to detect the presence of nucleic acid sequences in samples suspected of containing the same. In addition, the invention provides processes for making the probe and for detecting nucleic acids in test samples.

Those skilled in the art should note that the disclosure herein on particular embodiments of the present invention is exemplary only, and that various other alternatives, adaptations, and modifications may be made within the scope of the present invention. Accordingly, the present invention is not limited to the specific embodiments as illustrated herein, and is embodied in the claims appended hereto.

What is claimed is:

1. A process for labeling a single-stranded nucleic acid which comprises the steps of:
   (a) contacting the nucleic acid with one or more labeling compositions of the formula:

[A]―[B]―L wherein A is an alkylating moiety, B is a divalent organic moiety having the formula:

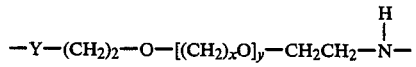

where Y is O, NH or N—CHO, x is a number from 1 to 4 and y is a number from 2 to 4, and L is a monovalent label moiety, wherein B is exclusive of any portion of the alkylating and label moieties, said contacting occurring so as to cause the alkylating moiety of the labeling composition to complex with the nucleic acid; and (b) activating the complex so as to induce the alkylating moiety to bond covalently to the nucleic acid.

2. The process of claim 1 wherein the nucleic acid is DNA and the label moiety is non-radioactive.

3. The process of claim 1 wherein A is of the formula:

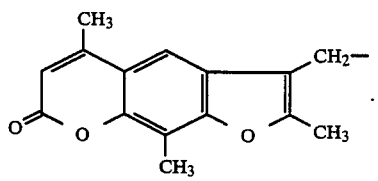

4. A process for preparing a labeled single-stranded nucleic acid hybridization probe for detecting homologous nucleic acid sequences which process comprises the steps of:

(a) contacting a single-stranded nucleic acid comprising a single-stranded region capable of hybridization with the nucleic acid sequence to be detected, with at least one of the labeling compositions of the formula:

[A]―[B]―L wherein A is an alkylating moiety, B is a divalent organic moiety having the formula:

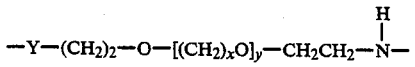

where Y is O, NH or N—CHO, x is a number from 1 to 4 and y is a number from 2 to 4, and L is a monovalent label moiety, wherein B is exclusive of any portion of the alkylating and label moieties, said contacting causing the alkylating moiety of the labeling composition(s) to complex with the nucleic acid; and (b) activating the complex to induce the alkylating moiety to bond covalently to the nucleic acid.

5. The process of claim 4 wherein A of the labeling compound is of the formula:

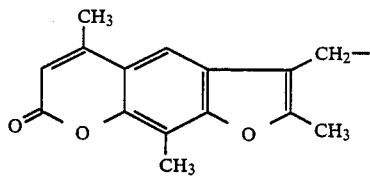

and the activating step (b) is carried out by irradiating the complex with ultraviolet light.

6. The process of claim 4 wherein the nucleic acid is DNA and L is detectable by spectroscopy, photochemistry, or by biochemical, immunochemical or chemical means.

7. The process of claim 4 wherein step (a) is carried out by incubating the nucleic acid with the labeling composition in a medium at about 0° to 50° C. containing a buffer with a pH of between about 6 and 9.

8. The process of claim 7 wherein the medium is at about 4° to 20° C. and the pH is between about 6 and 8.

9. The process of claim 5 wherein step (b) is carried out using ultraviolet light of from about 350 to 390 nm wavelength.

10. The process of claim 9 wherein the wavelength is about 360 nm and the step is carried out at from 1 to 100 mWatts per cm² for from one minute to 15 hours.

11. A process for preparing a labeled single-stranded DNA hybridization probe for detecting homologous DNA sequences which process comprises the steps of:

(a) inserting a DNA fragment which contains a sequence complementary to the sequence to be detected into the bacteriophage M13 genome at a restriction site therein and preparing therefrom circular single-stranded DNA containing the DNA fragment;

(b) contacting the DNA from step (a) with at least one labeling composition of the formula:

[A]―[B]―L wherein A is an alkylating moiety, B is a divalent organic moiety having the formula:

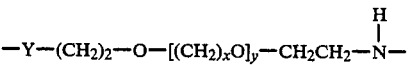

where Y is O, NH or N—CHO, x is a number from 1 to 4 and y is a number from 2 to 4, and L is a monovalent label moiety, wherein B is exclusive of any portion of the alkylating and label moieties, said contacting causing the alkylating moiety of the labeling composition(s) to complex with the DNA; and (c) activating the complex to induce the alkylating moiety to bond covalently to the single-stranded DNA.

12. The process of claim 11 wherein A of the labeling composition is of the formula:

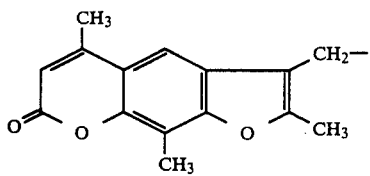

the label moiety is non-radioactive, and the activating step (c) is carried out by irradiating the complex with ultraviolet light.

13. The process of claim 12 wherein the labeling composition is of the formula:

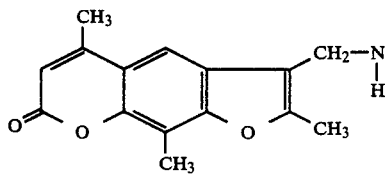

14. The process of claim 12 wherein the labeling composition is of the formula:

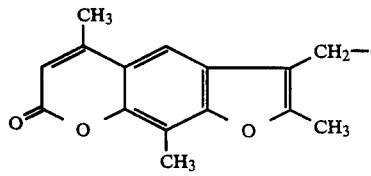

15. A labeled single-stranded nucleic acid hybridization probe for detecting homologous nucleic acid sequences comprising a single-stranded region capable of hybridization with the nucleic acid sequence to be detected adjacent to a single-stranded region not capable of such hybridization, said probe being covalently bound to at least one alkylating moiety, which is in turn bound to a divalent organic moiety having the formula:

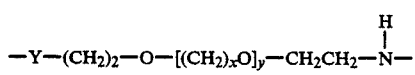

where Y is 0, NH or N—CHO, x is a number from 1 to 4 and y is a number from 2 to 4, which organic moiety is in turn bound to a monovalent label moiety, wherein said divalent organic moiety is exclusive of any portion of the alkylating and label moieties.

16. The probe of claim 15 wherein the alkylating moiety is a 4'-methylene-substituted-4,5',8-trimethylpsoralen moiety and the label moiety is detectable by spectroscopy or photochemistry or by formation of a detectable complex between the label moiety and a polypeptide, lectin or antibody with or without an enzyme associated therewith.

17. The probe of claim 16 wherein the bound conjugate of divalent organic moiety and monovalent label moiety has the formula:

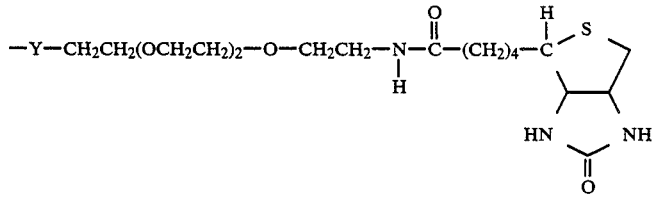

wherein Y is NH.

18. The probe of claim 15 wherein the nucleic acid is DNA.

19. The probe of claim 15 wherein the nucleic acid sequence to be detected is characteristic of a pathogenic microbe, is in a gene involved in HLA typing, is an amplified oncogene, or is associated with a genetic or infectious disease.

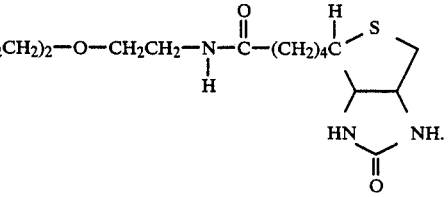

20. A complex comprising the probe of claim 19 and a polypeptide, lectin, or antibody capable of forming a complex with the label moiety of said probe.

21. The complex of claim 20 wherein the polypeptide, lectin or antibody includes a detectable moiety selected from the group consisting of a fluorescent dye, an electron dense reagent, or an enzyme capable of depositing a reaction product.

22. A complex comprising the probe of claim 19 containing biotin as the label moiety and a conjugate of streptavidin and a peroxidase.

23. A process for detecting the presence of one or more nucleic acid sequences in a sample suspected of containing the sequence or sequences comprising:

(a) contacting the sample with an effective amount of reagent sufficient to open the cells, animal cell membranes, body fluids, viral capsids, bacterial cell walls, bacterial membranes, or tissues of the sample and to expose and separate the strands of the nucleic acid or acids in the sample;

(b) contacting the exposed and separated strands with an effective amount of the hybridization probe of claim 15 under hybridization conditions; and (c) detecting whether hybridization of homologous nucleic acid sequences to the probe has occurred by means of the label moiety on the probe.

24. A process for detecting the presence of one or more nucleic acid sequences in a sample suspected of containing the sequence or sequences comprising:
(a) contacting the sample with an effective amount of reagent sufficient to open the cells, animal cell membranes, body fluids, viral capsids, bacterial cell walls, bacterial membranes, or tissues of the sample and to expose and separate the strands of the nucleic acid or acids in the sample;
(b) depositing the sample before, during, or after step (a) on an inert support;
(c) contacting the deposited sample with an effective amount of reagent sufficient to affix a substantially single-stranded form of the nucleic acid or acids on the support;
(d) contacting the affixed nucleic acid single-stranded form with an effective amount of the hybridization probe of claim 15 under hybridization conditions; and
(e) detecting hybridization of any homologous single-stranded nucleic acid sequences by means of the label moiety on the probe.

25. The process of claim 24 wherein the homologous sequence or sequences to be detected are characteristic of a pathogenic microbe or are associated with an infectious disease.

26. A process for conducting HLA typing comprising:
(a) digesting genomic HLA DNA from an individual with a restriction endonuclease which produces a polymorphic digestion pattern with HLA DNA;
(b) subjecting the digestion products to gel electrophoresis;
(c) transferring the sample from step (b) to a membrane;
(d) contacting the sample with an effective amount of a base sufficient to expose the nucleic acids in the sample and to separate the strands of the nucleic acid or acids in said sample;
(e) neutralizing said sample;
(f) exposing said sample to UV light, a drying solvent, or heat to affix a substantially single-stranded form of the nucleic acid or acids in the sample on the membrane at about the same site on the membrane where the sample was deposited;
(g) contacting said affixed single-stranded DNA sample with an effective amount of a reagent which prevents nonspecific reaction of the membrane with the probe to be employed;
(h) contacting said affixed single-stranded DNA sample with an effective amount of the hybridization probe of claim 17 containing a single-stranded HLA gene as the hybridizing region under hybridization conditions;
(i) washing said sample of unhybridized probe;
(j) detecting hybridization of any homologous single-stranded nucleic acid sequence or sequences present in the sample by means of the label moiety on the probe; and
(k) comparing the detected products from step (j) with the restriction fragment pattern of a known sample and/or with molecular weight markers.

27. The process of claim 26 wherein step (j) is accomplished by contacting the probe with a conjugate of streptavidin and horseradish peroxidase, adding a peroxidase substrate and detecting visually the reaction product of peroxidase and substrate.

28. A marker mix comprising a mixture of two or more single-stranded nucleic acids of different lengths or specificities which are covalently bound to at least one alkylating moiety, which is in turn bound to a divalent organic moiety having the formula:

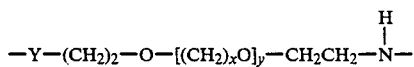

where Y is O, NH or N—CHO, x is a number from 1 to 4 and y is a number from 2 to 4, which organic moiety is in turn bound to a monovalent label moiety, wherein said divalent organic moiety is exclusive of any portion of the alkylating and label moieties.

* * * * *